United States Patent [19]
Ratcliffe et al.

[11] 4,326,081
[45] Apr. 20, 1982

[54] CONVERSION OF MONONITRO-AROMATIC COMPOUNDS TO AMINO COMPOUNDS BY HYDROGEN SULFIDE

[75] Inventors: Charles T. Ratcliffe, Morristown; Stuart L. Soled, Madison; Anthony J. Signorelli, Succasunna; Irving L. Mador, Morristown, all of N.J.

[73] Assignee: Allied Corporation, Morristown, N.J.

[21] Appl. No.: 237,326

[22] Filed: Feb. 23, 1981

[51] Int. Cl.$^3$ .............................................. C07C 85/11
[52] U.S. Cl. ................... 564/416; 564/417; 564/418
[58] Field of Search ............... 564/417, 418, 416, 423, 564/422, 420

[56] References Cited

U.S. PATENT DOCUMENTS

| | | | |
|---|---|---|---|
| 714,428 | 11/1902 | Wirth | 564/416 |
| 2,464,194 | 3/1949 | Zimmerman | 564/417 |
| 2,795,614 | 6/1957 | De Garmo et al. | 564/416 |
| 3,253,038 | 5/1966 | Wise | 564/416 |
| 3,254,125 | 5/1966 | Levy et al. | 564/417 |
| 3,929,891 | 12/1975 | Habig et al. | 564/417 |
| 4,115,652 | 9/1978 | Linhart et al. | 564/416 X |

FOREIGN PATENT DOCUMENTS

| | | | |
|---|---|---|---|
| 1410803 | 10/1964 | France | 564/416 |
| 7201425 | 10/1972 | Netherlands | 564/417 |
| 16407 | of 1895 | United Kingdom | 564/416 |

Primary Examiner—John Doll
Attorney, Agent, or Firm—Robert A. Harman; Alan M. Doernberg

[57] ABSTRACT

Hydrogenation of mononitroaromatic compounds, particularly nitrobenzene, nitrotoluene and their monochloro and monohydroxy ring substitution products, using hydrogen sulfide as reducing agent and a titanium dioxide catalyst at 200°–400° C. and atmospheric pressure.

11 Claims, No Drawings

CONVERSION OF MONONITROAROMATIC COMPOUNDS TO AMINO COMPOUNDS BY HYDROGEN SULFIDE

BACKGROUND OF THE INVENTION

This application relates to a process for vapor phase hydrogenation at reaction temperature in the range between 200° and 400° C. of a nitroaromatic compound, of the group consisting of nitrobenzene, nitrotoluene, and mono- and poly(chloro-, bromo, fluoro-)nitrobenzenes and nitrotoluenes, to the corresponding aminoaromatic compound comprising conducting said nitroaromatic compound with a catalyst consisting essentially of titanium dioxide.

It is known (Etzel, J. Physical Chem. Vol. 32, pages 852–860) that titanium dioxide is a good catalyst for reduction of nitrobenzene by hydrogen gas, especially at a temperature of about 300° C.

U.S. Pat. No. 3,253,038 of May 24, 1966 to Wise discloses use of hydrogen sulfide for reduction of nitrobenzene in either liquid phase at about 200° C. or vapor phase at about 300° C. and atmospheric pressure over a zeolite catalyst in the sodium form. In the examples, the conversion of nitrobenzene to aniline is quite low.

U.S. Pat. No. 3,255,252 of June 7, 1966 to Gold relates to liquid phase reduction of nitroaromatic compounds by hydrogen sulfide using, in a homogeneous catalysis process an amine catalyst; and in a heterogeneous catalysis, a combination of silica and amphoteric metal oxide such as alumina, thoria or zirconia. Again in this patent, a large part of the nitrobenzene charge is recovered unreacted, per the Examples.

U.S. Pat. No. 4,059,627 of Nov. 22, 1977 to Kritzler et al. discloses in column 1 that hydrogenation of chloroaromatic compounds is accompanied by more or less extensive dechlorination with accompanying loss of yield and high corrosiveness due to the hydrogen chloride formed. The patent cites prior art use of noble metal sulfides or sulfited noble metal catalysts. In the invention, a noble metal on a carbon support is used in presence of a small proportion of a thioether functioning as an inhibitor of the dechlorination (column 4, line 63—column 5, line 2). The temperatures disclosed are 30°–200° C. (column 5, line 45) and hydrogen pressure is 5–150 atmospheres (column 5, line 15).

U.S. Pat. No. 4,128,586 of Dec. 5, 1978 to Ratcliffe discloses catalytic reduction of aromatic sulfonyl halides with hydrogen sulfide, to form aromatic thiols.

SUMMARY

In accordance with the present invention, a mononitroaromatic compound of the group consisting of nitrobenzene, nitrotoluene, and mono(chloro-,bromo-,fluoro- and hydroxy-)nitrobenzene and nitrotoluenes is hydrogenated at reaction temperature in the range between 200° and 400° C. to the corresponding amino aromatic compound by use of hydrogen sulfide as the hydrogenation gas and using a catalyst consisting essentially of titanium dioxide.

DETAILED DESCRIPTION

Our invention applies most particularly to nitrobenzene. Using this compound, a reaction temperature of about 300° C. is optimum. It is found that the catalyst under these conditions becomes gradually less active. This effect is believed due to accumulation of liquid sulfur upon the catalyst surface; the activity can be restored by heating the catalyst in a stream of nitrogen at 400° C. or above. Desirably, to promote initial activity, the catalyst is exposed to hydrogen sulfide at about 400° C. before use.

Generally the pressure employed is about atmospheric but higher pressure can be employed, for example to obtain higher reaction rates at given temperature. Depending on pressure and temperature, the nitro compound may be either a vapor or liquid, or dissolved in a solvent.

In view of the need to reactivate the catalyst at a temperature at which liquid sulfur is vaporized, it is desirable to provide for moving the catalyst out of the reaction zone to a zone wherein the temperature is at least about 400° C., for example by circulating a fluid bed of catalyst from the reaction zone to a zone of higher temperature, and back.

Titanium dioxide can be used as obtained commercially for catalyzing the hydrogenation in our process. Such catalyst normally will contain small amounts of impurities which appear to be capable of conferring a higher activity than observed for very pure titanium dioxide. For similar reasons, it is desirable to modify the titanium dioxide catalyst with a metal sulfide, more particularly a sulfide of a transition metal, especially a metal sulfide of the group consisting of cobalt, ruthenium and palladium sulfides. The quantity of such modifying sulfide is desirably in the range of 0.001 to 10 percent by weight of metal based on the weight of the catalyst; more especially 0.5 to 5 percent by weight of metal based on the weight of the catalyst. Especially cobalt sulfide is a desirable modifier for the titanium dioxide catalyst of the invention.

Surface area measurements made on catalysts found active in the present study have shown values as low as 34 sq. m/g and as high as 284 sq. m/g. The activity of the catalyst is regarded as being proportional to the surface area, other things being equal.

The anatase crystalline form of titanium dioxide and a mixed anatose-rutile form showed similar activity. Hence overall crystal structure of the titanium dioxide catalyst does not appear to be critical.

The process of this invention has been found to be of value in the conversion of the nitro group in halogen-substituted and hydroxyl-substituted nitroaromatic compounds in particular chloronitrobenzenes, nitrophenols, and ring-substituted chloronitrotoluenes to the corresponding amino group. When using hydrogen sulfide and the titanium dioxide catalyst of the present invention, it is found that the problem of dechlorination of the chloro compounds, noted when using prior art reduction techniques, is avoided.

The examples which follow illustrate this invention and the best mode contemplated by the inventors for carrying out their invention, but are not to be interpreted in a limiting sense.

Procedure

The studies summarized in the Tables below were carried out in a vertical glass flow reactor which had been fabricated from a 10 mm O.D. glass tube. An electrically heated oven, 38.1 cm (15") in length with an I.D. of 12 mm, was placed concentrically around the glass tube during reactions and catalyst pretreatment. Dual inlet ports on the top of the reactor allowed gas and liquid feeds to be metered into the reactor. A preheater section in the top 10.16 cm (4") of the reactor tube contained inert quartz chips which allowed vaporization of liquid reactants. A 1.0 g catalyst sample, of volume 0.7 cc for TiO$_2$ samples, 18/30 mesh, was located in the center section of the reactor tube with a thermocouple probe taped to the exterior of the glass tube at the location of the catalyst. The reactor temperature was monitored with this external thermocouple probe and allowed an isothermal temperature to be maintained during extended reaction periods. An electric proportional controller was used to regulate the oven temperature. Liquid reactants were metered with a liquid syringe pump. The liquid feeds, which were controlled with mass flow controllers, were mixed with the gaseous reagents above the heated section of the reactor. Products were collected in bottles cooled by ice or solid carbon dioxide at the base of the reactor. Samples were usually collected over a 30-45 minute interval during a run. The exit line passed through a 20% caustic scrubber before being vented to the atmosphere.

The stoichiometric proportions of the reactants are given by: $3H_2S + PhNO_2 \rightarrow 2H_2O + PhNH_2 + 3S$. In the subject studies, no noticeable differences were found between use of 3:1 and 8:1 mole ratios of H$_2$S:nitrobenzene. The ratio used in the runs of the Tables below was 8:1.

Unless otherwise noted, the reaction temperature in the runs of the Tables was 300° C.

Product Analysis

Aniline, nitrobenzene, sulfur and water can readily be separated on many g.c. columns. A 3% Silar on Gas Chrom Q column, 3 mm×2 m ($\frac{1}{8}''\times 6'$), was generally used in this study to determine the relative conversion of nitrobenzene and the purity of the product. Mass spectral analysis on selected samples was used to detect and identify impurities as well as to initially establish the identity of the major products. Nitrobenzene and aniline separate into well defined peaks for quantitative analysis. (While sulfur and water also yielded well defined peaks, it was not possible to gain even qualitative analysis of these by-products due to sampling problems). A clean separation of the products from chloronitroaromatic reductions was achieved with 3% Silar columns.

TABLE 1

(Comparisons)
Reduction of Nitrobenzenes with Al$_2$O$_3$ Based Catalysts
(after 90 minutes on stream)

| Ex. | Catalyst* | Products (mole %) | |
|---|---|---|---|
| | | Aniline | Nitrobenzene |
| 1. | OsS$_x$ on Al$_2$O$_3$ | 32.9 | 65.9 |
| 2. | RuS$_x$ on Al$_2$O$_3$ | 27.5 | 72.5 |
| 3. | IrS$_x$ on Al$_2$O$_3$ | 43.4 | 56.6 |
| 4. | FeS$_x$ on Al$_2$O$_3$ | 23.2 | 76.2 |
| 5. | NiS$_x$ on Al$_2$O$_3$ | 18.3 | 81.7 |
| 6. | PdS$_x$ on Al$_2$O$_3$ | 24.4 | 75.6 |
| 7. | PtS$_x$ on Al$_2$O$_3$ | 23.0 | 75.3 |
| 8. | V$_2$O$_5$ on Al$_2$O$_3$ | 22.3 | 77.7 |

*All catalysts wet impregnated with the metal chloride or nitrate salts to yield 2% metal on Harshaw 0104 Al$_2$O$_3$, 18/30 mesh support. Runs were at 300° C.

TABLE 2

Reduction of Nitrobenzene with TiO$_2$ Based Catalysts

| Ex. | Catalyst* | Time On Stream (min) | Products (mole %) | |
|---|---|---|---|---|
| | | | Aniline | Nitrobenzene |
| 1. | RuS$_x$ on TiO$_2$ | 180 | 100.0 | — |
| | | 260 | 56.1 | 43.3 |
| 2. | RhS$_x$ on TiO$_2$ | 90 | 100.0 | — |
| | | 180 | 82.2 | 17.7 |
| | | 225(a) | 100.0 | — |
| | | 360(a) | 100.0 | — |
| 3. | IrS$_x$ on TiO$_2$ | 40 | 100.0 | — |
| | | 170 | 53.5 | 45.8 |
| | | 220(a) | 78.9 | 20.4 |
| 4. | FeS$_x$ on TiO$_2$ | 90 | 100.0 | — |
| | | 170 | 75.5 | 24.5 |
| 5. | CoS$_x$ on TiO$_2$ | 235 | 100.0 | — |
| | | 325 | 85.4 | 14.6 |
| | | 625 | 100.0 | — |
| 6. | OsS$_x$ on TiO$_2$ | 85 | 100.0 | — |
| | | 180 | 73.3 | 26.7 |
| | | 270(a) | 100.0 | — |
| 7. | NiS$_x$ on TiO$_2$ | 45 | 100.0 | — |
| | | 135 | 80.7 | 19.3 |
| 8. | PdS$_x$ on TiO$_2$ | 180 | 100.0 | — |
| | | 270 | 86.2 | 13.7 |
| | | 330(a) | 100.0 | — |
| 9. | PtS$_x$ on TiO$_2$ | 45 | 100.0 | — |
| | | 180 | 48.1 | 51.9 |
| | | 285(a) | 83.8 | 16.2 |
| 10. | V$_2$O$_5$ on TiO$_2$ | 45 | 100.0 | — |
| | | 180 | 73.4 | 26.5 |
| | | 315(a) | 100.0 | — |
| | | 540(a) | 98.6 | 1.4 |
| 11. | TiO$_2$ | 30 | 97.9 | 2.1 |
| | | 90 | 44.2 | 55.8 |
| 12. | 0.12% Co on TiO$_2$ (Harshaw 0404) | 270 | 100.0 | — |
| | | 390 | 92.3 | 7.7 |
| 13. | 0.12% CoS$_x$ on TiO$_2$ | 214 | 100.0 | — |
| | | 300 | 86.9 | 13.1 |
| 14. | 0.2% RuS$_x$ on TiO$_2$ | 205 | 100.0 | — |
| | | 300 | 97.7 | 2.259 |
| 15. | 0.02% RuS$_x$ on TiO$_2$ | 315 | 100.0 | — |
| | | 300 | 94.7 | 5.3 |
| 16. | TiO$_2$ (1) (Harshaw 0404) | 270 | 100.0 | — |
| | | 350 | 98.0 | 2.0 |
| 17. | TiO$_2$ (2) (Harshaw 0404) | 35 | 79.6 | 20.4 |
| | | 70 | 43.3 | 56.7 |
| | | 140 | 33.1 | 66.9 |
| | | 170(b) | 100.0 | — |
| | | 400 | 100.0 | — |
| 18. | TiO$_2$ (3) (air treated) Harshaw 0404 | 35(c) | 75.1 | 24.9 |
| | | 100 | 35.9 | 64.1 |
| 19. | TiO$_2$ (4) | 145 | 100.0 | — |
| | | 230 | 95.0 | 5.0 |
| | | 320 | 77.9 | 22.1 |
| | | 625 | 56.5 | 43.5 |
| | | 670(a) | 92.6 | 7.4 |
| | | 880(c) | 100.0 | — |
| | | 960 | 92.5 | 7.5 |
| | | 1140(c) | 100.0 | — |
| | | 1260 | 82.5 | 17.7 |
| 20. | TiO$_2$ (4) | 240 | 100.0 | — |
| | | 280 | 59.6 | 40.0 |
| | | 430 | 100.0 | — |

*Unless otherwise designated, all catalysts were wet impregnated with chloride or nitrate salts to yield 2.5% metal on Harshaw TiO$_2$-0404 support. 1.0 g samples of each catalyst were heat treated at 500° C., then sulfided at 400° C. prior to testing.
(a) After treating the catalyst with an N$_2$ stream at 400° C. for 45 minutes.
(b) Treated with N$_2$ at 500°C., 1 hour.
(c) After treatment with air at 400° C., 30 minutes, then H$_2$S flow at 300° C.
(1) TiO$_2$ particles, 18/30 mesh, were soaked in deionized H$_2$O, dried under vacuum at 80° C., heated to 400° C. in N$_2$ stream containing 40% H$_2$S for 60 minutes, then cooled to 300° C.
(2) TiO$_2$ particles, 18/30 mesh, heated to 400° C. in 40% H$_2$S stream for 60 minutes, cooled to 300° C.
(3) TiO$_2$ was heated in air at 500° C. for 1 hour, followed by sulfiding at 400° C.
(4) Used TiO$_2$ sample from run #152-22, reloaded, heated in 40% H$_2$S at 400°C., 1 hour.

TABLE 3

Reduction of Substituted Nitroaromatics with H₂S
(Over TiO₂ Harshaw 0404 catalyst)

| Ex. | Reactant | Temp °C | Conv. % | Products (mole %) (a) | (b) | (c) |
|---|---|---|---|---|---|---|
| 1. | O-ClPhNO$_2$ | 300 | 100 | 0.02 | 99.98 | — |
| 2. | m-BrPhNO$_2$ | 300 | 100 | 0.035 | 99.96 | — |
| 3. | p-MePhNO$_2$ | 300 | 100 | — | | |
| 4. | p-ClPhNO$_2$ | 270 | 100 | 2.63 | | |
|  |  | 240 | 100 | 0.107 | | |
|  |  | 180 | 57 | — | | |
| 5. | m-ClPhNO$_2$ | 300 | 100 | 0.008 | | |
| 6. | 1-Me-2-Cl-3-(NO$_2$)Ph | 300 | 100 | — | | |
| 7. | p-Cl-PhNO$_2$ | 100 (d) | 6.83 | — | | |
| 8. | p-HOPhNO$_2$ | 300 | 100 | — | | |
| 9. | p-HOPhNO$_2$ | 300 | 74.5 | — | | |
| 10. | o-HOPhNO$_2$ | 300 | 94.3 | — | | |

(a) = PhNH$_2$;
(b) = XPhNH$_2$;
(c) = XPhNO$_2$ where X = Cl, Br or OH;
(d) liq. phase, 60 p.s.i. H$_2$S, 100° C.

In commercial operations, as previously mentioned, provision should be made for moving the catalyst from the reaction zone to a reactivation zone maintained at temperature of at least about 400° C., and back to the reaction zone. This can be accomplished by conventional means such as using fluid bed technology.

We claim:

1. In a process for hydrogenation at reaction temperature in the range between 200° and 400° C. of a mononitroaromatic compound, of the group consisting of nitrobenzene, nitrotoluene, and mono(chloro-, bromo-, fluoro- and hydroxy-) nitrobenzenes and nitrotoluenes, to the corresponding aminoaromatic compound comprising contacting said compound with a catalyst consisting essentially of titanium dioxide: the improvement which comprises employing hydrogen sulfide as the hydrogenation gas.

2. Process of claim 1 wherein said catalyst contains from 0.001 to 10 weight percent of a transition metal sulfide.

3. Process of claim 1 wherein said nitroaromatic compound is nitrobenzene.

4. Process of claim 3 wherein the titanium dioxide catalyst is modified with a metal sulfide of the group consisting of cobalt, ruthenium, and palladium sulfides.

5. Process of claim 4 wherein the proportion of metal sulfide is in the range of 0.001 to 10 percent by weight of metal based on the weight of the catalyst.

6. Process of claim 4 wherein the metal is cobalt and is in the range of 0.05 to 5 percent by weight of the catalyst.

7. Process of claim 3 wherein the reaction temperature is about 300° C. and wherein the catalyst is moved out of the reaction zone to a zone wherein the temperature is at least 400° C.

8. Process of claim 1 wherein the mononitroaromatic compound is a ring-substituted monochloronitroaromatic compound.

9. Process of claim 8 wherein the mononitroaromatic compound is a chloronitrobenzene.

10. Process of claim 1 wherein the nitroaromatic compound is a nitrotoluene.

11. Process of claim 1 wherein the nitroaromatic compound is a nitrophenol.

* * * * *